US00PP12545P2

(12) United States Plant Patent
Drewlow

(10) Patent No.: US PP12,545 P2
(45) Date of Patent: Apr. 16, 2002

(54) NEW GUINEA IMPATIENS PLANT NAMED 'OVATION ROSE SWIRLS'

(75) Inventor: Lyndon W. Drewlow, Santa Barabara County, CA (US)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 09/550,517

(22) Filed: Apr. 17, 2000

(51) Int. Cl.[7] ..... A01H 5/00
(52) U.S. Cl. ..... Plt./318
(58) Field of Search ..... Plt./318

(56) References Cited

U.S. PATENT DOCUMENTS

PP11,284 P * 3/2000 Dummen ..... Plt./318

OTHER PUBLICATIONS

UPOV–ROM GTITM Computer Database, 2001/02, GTI Jouve Retrieval Software, citation for 'Ovation Rose Swirls'.*

* cited by examiner

*Primary Examiner*—Bruce R. Campell
*Assistant Examiner*—Susan B. McCormick
(74) *Attorney, Agent, or Firm*—Webb Ziesenheim Logsdon Orkin & Hanson, P.C.

(57) ABSTRACT

A distinct cultivar of Impatiens plant named Ovation Rose Swirls, characterized by its two-toned rose colored flowers, large flower diameter, dark green leaves with cream colored variegation, continuous, and long-lasting flowering, self-branching and vigorous habit.

1 Drawing Sheet

The present invention relates to a new and distinctive cultivar of Impatiens plant botanically known as Impatiens, commercially known as New Guinea Impatiens, and known by the cultivar name 'Ovation Rose Swirls'. Ovation Rose Swirls was developed in a controlled breeding program by crossing Mikkelsen Seedling No. 92-503-1 (seed parent) with Mikkelsen Seedling No. 93-1019-7 (pollen parent). The seed and pollen parents are proprietary breeding lines which have not been sold or made publicly available in this country.

Asexual reproduction carried out by the inventor in Lompoc, Calif. by terminal or stem cuttings has shown that the unique features of this new Impatiens are stabilized and are reproduced true to type in successive propagations.

The following combination of characteristics distinguishes the new Impatiens from both its parent varieties and other cultivated Impatiens of this type known to the inventor and used in the floriculture industry:

1. Ovation Rose Swirls has two-tone rose colored flowers with Red-Purple Group 64D near the center of the flower and Red-Purple Group 66C at the edge. 'Kallima'(U.S. Plant Pat. No. 9,146) has Red-Purple Group 65A near the center of the flower and Red-Purple Group 68B near the edge, and 'Harmony Light Pink' (unpatented), is Red-Purple Group 62D near the center of the flower and Red-Purple Group 62C near the edge.

2. 'Ovation Rose Swirls' does not have carmine color of Red-Purple Group 67B at center of flowers as do 'Kallima' and 'Harmony Light Pink'.

3. 'Ovation Rose Swirls' has a large flower diameter (7.0 to 7.5 cm), as compared to 'Kallima' and 'Harmony Light Pink' (6.0 to 6.5 cm).

4. 'Ovation Rose Swirls' has a cream variegation around the midrib near the basal part of mature leaves, as compared to 'Kallima' and 'Harmony Light Pink', which are not variegated.

5. 'Ovation Rose Swirls' has intermediate leaf coloration of dark green while 'Kallima' has dark green leaves with a red-purple cast and 'Harmony Light Pink' has bright green leaves.

6. 'Ovation Rose Swirls' has a more mounded growth habit as compared to 'Kallima' and 'Harmony Light Pink', which are more upright in growth habit.

7. 'Ovation Rose Swirls' has a shorter leaf (9 to 10 cm) with an oval appearance, whereas, 'Kallima' and 'Harmony Light Pink' have a longer (11 to 12 cm), lanceolate-shaped leaf.

8. 'Ovation Rose Swirls' has a yellow-green pedicel while both 'Kallima' and 'Harmony Light Pink' have red-purple pedicels.

9. 'Ovation Rose Swirls' has a light red-purple spur with a green tip, as compared with 'Kallima' and 'Harmony Light Pink', which have deep red-purple spurs with red-purple tips.

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. The plants were grown at 16° C. night temperatures, under 3000 to 4000 foot candles of light and with nutritional trace elements added. Habit of growth, foliage coloration, leaf variegation, size of leaves and flower size will be greatly influenced by nutritional and environmental conditions.

Color references are made to The Royal Horticultural Society Colour Chart except where general terms of ordinary significance are used.

Botanical classification: *Impatiens hawkeri.*

Parentage: A controlled cross between female parent, Mikkelsen Seedling No. 92-503-1 and male parent Mikkelsen Seedling No. 93-1019-7.

Propagation:

(*A*) *Type cutting.*—Stem tip 15 mm long will develop to 4 to 5 cm long in 18 to 21 days.

(*B*) *Time to root*—8–10 days at 23° C. summer; 10–12 days at 20° C. winter.

(*C*) *Rooting habit.*—Heavy, fibrous.

Plant description:

(*A*) *Height.*—18 to 22 cm.

(*B*) *Width.*—40 to 45 cm.

(*C*) *Form and habit of growth.*—Mounded, self-branching, intermediate in height, flowers open over the top of leaf canopy; continuous flowering; vigorous growing flowering herb (a non-woody stemmed plant that dies completely at the end of the growing season.) Internode length: Lateral branches: Average length of 15 to 18 cm (highly variable); average diameter of 5 to 7 mm; Yellow-Green Group 146B with Greyed-Purple Group 184B cast. Stem: Length of 21 to 25 cm (highly variable); diameter of 8 to 10 mm; Yellow-Green Group 146 B with Greyed-Purple Group 184B cast.

(*D*) *Foliage description.*—Deep green with cream variegation around the midrib; widest at the base of the petal with red-purple cast to the midrib. (1) Size: 9 to 10 cm long and 3.5 to 4.0 cm wide on average mature leaf. (2) Shape: Lanceolate to oval with acuminate apex and acute base. (3) Texture: Both upper and lower surfaces are glabrous. (4) Margin: Entire, with fine ciliate. (5) Color: Young foliage, top side is Yellow-Green Group 147A with no variegation, underside is Yellow-Green Group 147A with red-purple cast. Mature foliage, top side is Yellow-Green Group 147A with Yellow-Green Group 153B to 153C variegation, underside is Yellow-Green Group 147A with Greyed-Red Group 182A cast. Area of variegation increases in brighter light of summer but color stays the same. (6) Veination: Pinnate with Yellow-Green Group 146D veins. (7) Leaf arrangement: Whorl — usually 5 leaves in a whorl. (8) Petiole: Length of 1.5 to 2 cm; diameter of 3 mm; Greyed-Purple Group 184D.

Flowering description:

(*E*) *Flowering habits.*—Flowers continuously from leaf whorl in a progressively orderly manner with one flower per leaf axil. When the last flower in a whorl opens, the first flower in the leaf whorl above starts to open. It takes 5 to 7 days for a mature bud to fully open and the flower may last two weeks or longer depending on the environment.

(*F*) *Natural flowering season.*—Indeterminate and continuous; quantity of flowering increases with increasing levels of light.

(*G*) *Flower bud.*—Ellipsoidial; flowers perfect; spur has Red-Purple Group 62B cast with a Yellow-Green Group 146C tip and is 4.0 cm long on mature bud with the throat behind the ovary and originating from the major sepal. Length: 16 to 18 mm; diameter: 13 mm. Shape: Ellipsoidal. Color: Red-Purple Group 63A just before opening.

(*H*) *Flowers borne.*—On individual Yellow-Green Group 147D pedicels 4.0 cm long from a whorl of usually five leaves. Flowering progressively around the whorls as buds and leaves develop. Leaf axils have one flower each.

(*I*) *Quantity of flowers.*—Numerous because of self-branching nature of plant and the long-lasting flower characteristic.

(*J*) *Diameter of flower.*—7.0 to 7.5 cm.

(*K*) *Petals.*—(1) Shape: Heart, standard is largest petal. (2) Color: Top side when opening is Red-Purple Group 64D at center of flower and radiating out into petals with Red-Purple Group 66C petal edge; fading to the larger area of Red-Purple Group 64D; underside is Red-Purple Group 65A. (3) Number of petals: Five. (4) Size of petals: Standard: 5.0 cm wide and 3.0 cm long, two equal lobes with shallow cut. Wings: 4.0 cm wide and 3.0 cm long, two unequal lobes with moderate cut. Keel: 4.0 cm wide and 3.5 cm long, two unequal lobes with moderate cut. (5) Texture: Smooth, satin-like.

(*L*) *Reproductive organs.*—(1) Stamens: Five in number. (a) Anther: Hooded shape, color is cream with red-purple cast. (b) Pollen color: Yellow-White Group 158C. (2) Pistils: (a) Stigma: Five, segmented column, White Group 155C with Red-Purple Group 60A cast. (b) Style color: White Group 155C. (c) Ovaries: Five in number, size is 6 mm when immature, color is [dark green] Yellow-Green Group 146A with Red-Purple Group 60A cast.

Disease resistance: No significant disease or insect problems seen to date.

Fruit/seed production: Plants are fertile but do not normally set seed under greenhouse or garden conditions unless in a controlled breeding program.

OTHER IMPORTANT CHARACTERISTICS

1. Self-branching, early flowering nature allows cultivar to be grown in 10 cm pots but is also very vigorous enough to be grown in 15 to 25 cm containers as well.

2. Minimal fading of older flowers and large overlapping petals result in a round flower that produces an attractive floral display.

3. Has shown the ability to tolerate both high temperatures and full sun and continue to bloom as demonstrated in Connellsville, Pa. summer trials and to bloom as well with cool night temperatures (5 to 10° C.) as demonstrated in outdoor trials in Lompoc, Calif., thus, extending the growing season.

I claim:

1. A new and distinct variety of Impatiens plant named Ovation Rose Swirls, as illustrated and described.

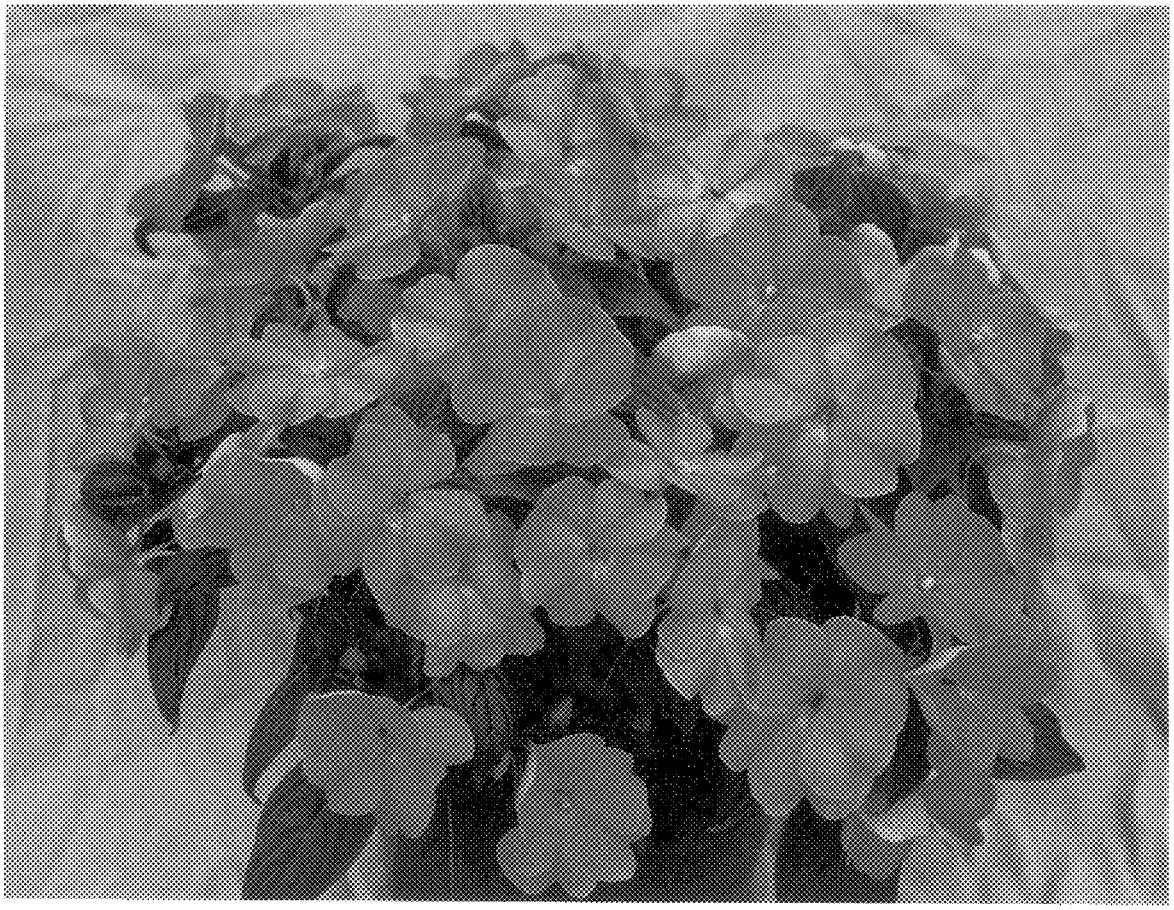

* * * * *